United States Patent [19]
Braun et al.

[11] Patent Number: 5,277,056
[45] Date of Patent: Jan. 11, 1994

[54] PROCESS AND APPARATUS FOR CONTINUOUSLY MONITORING WASTE GAS FROM AN INCINERATOR PLANT

[75] Inventors: Hartmut Braun; Andreas Gerig, both of Karlsruhe, Fed. Rep. of Germany

[73] Assignee: Kernforschungszentrum Karlsruhe GmbH, Fed. Rep. of Germany

[21] Appl. No.: 709,669

[22] Filed: Jun. 3, 1991

[51] Int. Cl.$^5$ .................. G01N 1/10; G01N 1/34
[52] U.S. Cl. .................. 73/23.31; 73/863.11; 423/21; 436/81
[58] Field of Search ............ 73/23.31, 863.11, 863.12; 423/210; 436/88, 81

[56] References Cited

U.S. PATENT DOCUMENTS

| | | | |
|---|---|---|---|
| 3,677,696 | 7/1972 | Bryk et al. | 423/210 |
| 3,764,496 | 10/1973 | Hultman et al. | 423/210 |
| 3,849,537 | 11/1974 | Allqulin | 423/210 |
| 4,141,702 | 2/1979 | de Vries | 423/210 |
| 4,195,524 | 4/1980 | Hansen | 73/863.11 |
| 4,233,274 | 11/1980 | Allgulin | 423/210 |
| 4,336,722 | 6/1982 | Schweitzer | 73/863.12 |
| 4,443,417 | 4/1984 | Wiklund | 423/210 |
| 4,640,751 | 10/1985 | Dyvik et al. | 423/210 |

FOREIGN PATENT DOCUMENTS

| | | |
|---|---|---|
| 0122248 | 10/1984 | European Pat. Off. . |
| 0172521 | 2/1986 | European Pat. Off. . |
| 3704533 | 8/1988 | Fed. Rep. of Germany . |
| 3803173 | 8/1989 | Fed. Rep. of Germany ........ 436/81 |

*Primary Examiner*—Hezron E. Williams
*Assistant Examiner*—Nashmiya Ashraf
*Attorney, Agent, or Firm*—Sughrue, Mion, Zinn, Macpeak & Seas

[57] ABSTRACT

Process for the continuous monitoring of waste gas from an incinerator plant, which contains volatile mercury halides and optionally metallic mercury in the form of vapor, with respect to the entire mercury content, of the waste gas taking a continuous test gas stream from the waste gas, cooling the test gas stream to form a condensate which contains a reducing agent, continuously passing the test gas stream into contact with the condensate to reduce the mercury halides contained in the test gas stream to metallic mercury by the reducing agent contained in the condensate, and subsequently determining the entire metallic mercury content by analysis of the test gas stream.

7 Claims, 2 Drawing Sheets

PROCESS AND APPARATUS FOR CONTINUOUSLY MONITORING WASTE GAS FROM AN INCINERATOR PLANT

BACKGROUND OF THE INVENTION

The present invention relates to a process for the continuous monitoring of waste gas, (flue gas) from an incinerator plant, which contains volatile mercury halides and optionally metallic mercury in the form of vapor, with respect to their entire mercury content, and an apparatus to carry out the process.

Continuous monitoring is possible only when mercury occurs in its metallic (elemental) form.

A process for continuously monitoring such waste gases is known from DE-OS 37 04 533.

In the process disclosed in DE-OS 37 04 533, a continuous sample of gas stream is taken from the waste gas and guided through an activated charcoal bed at a temperature of approximately 350° C. to reduce the volatile mercury halides.

In so doing, mercury halides, in particular $HgCl_2$, are reduced on the activated charcoal into metallic mercury. The entire mercury content in the waste gas is then determined by measuring the metallic mercury content in the so pretreated sampling stream.

The drawback with this process is that impure substances, which prevent the reduction of the mercury or its release from the activated charcoal bed or reoxidize the already reduced mercury, can accumulate in the activated charcoal.

For this reason, the process can be used only with a so-called clean gas, in particular with hydrogen chloride concentrations below 100 mg/m³. Furthermore, the activated charcoal must be replaced from time to time.

Furthermore, it is known to guide the test gas (sample gas) stream, instead of through an activated charcoal bed, through a tin(II)-chloride solution or through a boron hydride solution, where mercury halides are also reduced to metallic mercury.

Such a process requires a continuous metering of reducing agents. In this process, the reductant content in the solution must be continuously monitored.

Furthermore, an alternative process can be derived from the aforementioned published DE-OS 37 04 533, in which process any and all kinds of reducing agents are dispensed with and in which the mercury halides are reduced at a temperature of over 700° C. In so doing, existing hydrogen chloride must be set or reacted with calcium compounds. The high processing temperature makes the process time consuming.

SUMMARY OF THE INVENTION

An object of the present invention is to provide a process for the continuous monitoring of all mercury emission of the waste gases from an incinerator plant, primarily a refuse incinerator plant.

A further object of the present invention is to provide such a process that does not exhibit the drawbacks of known methods.

Another object of the present invention is to provide such a process which is conductible without external reducing agents and which does not require high temperatures.

A further object of the present invention is to provide such a process in which mercury halides, in particular the volatile mercury chlorides and bromides, are reliably reduced to metallic mercury (Hg).

An additional object of the present invention is to provide such a process which is largely independent of the composition of the incineration waste gases.

A still further object of the present invention is to provide such a process in which the mercury emission limits of e.g. 100 $\mu g/m^3$ for mercury compounds that are specified in the specifications concerning clean air regulations are to be reliably monitorable.

Another object of the present invention is to provide an apparatus to carry out the process.

To achieve the foregoing objects and in accordance with its purpose, the present invention provides a process for the continuous monitoring of waste gas from an incinerator plant, which contains volatile mercury halide and optionally metallic mercury in the form of vapor, with respect to the entire mercury content of the waste gas, comprising:

a) taking a continuous test gas stream from the waste gas, b) cooling the test gas stream to form a condensate which contains a reducing agent, c) continuously passing the test gas stream into contact with the condensate to reduce the mercury halides contained in the test gas stream to metallic mercury by the reducing agent contained in the condensate, and subsequently d) determining the entire metallic mercury content by analysis of the test gas stream after it is passed the condensate.

Preferably, the test gas stream is cooled in the cooling chamber to a temperature of from 1° to 30° C. It is also preferred to maintain the condensate at a pH value of at least 3 and at most 8.

The present invention also provides an apparatus for the continuous monitoring of waste gas from an incinerator plant, which contains volatile mercury halide and optionally metallic mercury in the form of vapor, comprising:

a) a cooling chamber for cooling and condensing a test gas stream taken from the waste gas, and for holding condensate which forms from the condensing of the test gas stream, b) means for holding constant the filling level of condensate in the cooling chamber, c) a supply line for introducing the test gas stream into the cooling chamber, and d) a gas line which connects the cooling chamber above the condensate filling level to a mercury analyzer.

Preferably, the means to hold the filling level constant is an overrun.

It is also preferred that the end of the supply line for the test gas stream is in the form of a gas filter and is located below the filling level that is held constant.

It is to be understood that both the foregoing general description and the following detailed description are exemplary and explanatory, but are not restrictive of the invention.

DETAILED DESCRIPTION OF THE INVENTION

Figure 2:
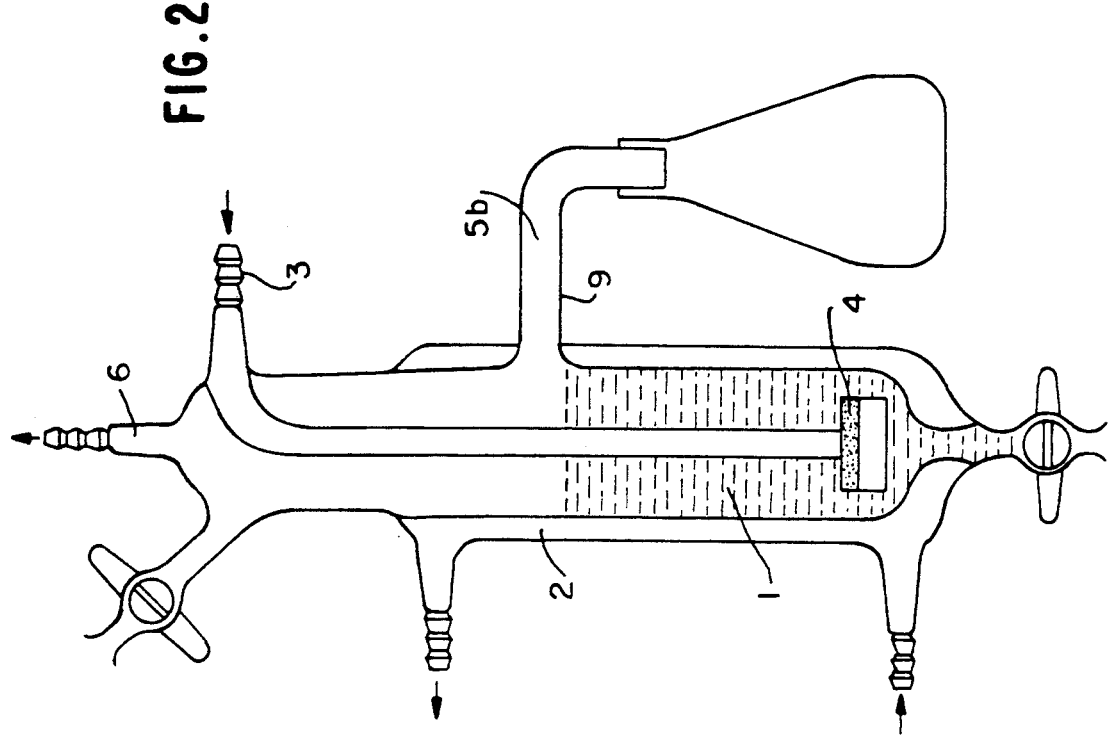
FIG. 2 shows another embodiment of an apparatus according to the present invention for carrying out the process according to the present invention.

The process according to the invention is characterized by the fact that the mercury halides in the test gas stream are reduced solely by existing reducing components which are present in the test gas stream. Tests indicate that the dust particles, present in the waste gas, and the $SO_2$ content of the waste gas are in a position to reduce in liquid phase the mercury halides to metallic mercury. Thus, the process of the present invention can be performed without the addition of external reducing agents.

According to the present invention, a sample of the waste gas stream (test gas stream) is cooled to the extent that a condensate is formed. In principle, it suffices to reduce the temperature of the test gas stream only to the extent that condensation takes place. However, it is more advantageous to select a temperature of from 1° to 30° C. Within this range, the best results are obtained at low temperatures, ranging from about 1° to 15° C. Thus, in the present invention, high temperatures are not necessary.

The test gas stream contains a non-condensable portion which is not condensed in the cooling chamber and which exits the cooling chamber after passing through the condensate.

The gaseous test gas stream from the supply line is continuously fed into the cooling chamber and after entering the cooling chamber is held or maintained continuously in contact with the formed condensate. In so doing, the entering test gas stream cools until a fresh condensate is generated so that there is a continuous generation of fresh condensate.

As discussed above, the condensate contains substances which are in a position to reduce existing mercury halides to metallic mercury. Due to the fact that continuously fresh condensate is generated, a sufficient reducing effect remains continuously in existence.

In general, the condensate will exhibit a pH value in the slightly acid range. When the condensate is very acidic, as in the case, e.g., in refuse incinerator plants, where highly chlorine-containing substances are burned, the pH value should be set or adjusted to between 3 and 8 e.g. by adding an alkaline compound. Especially preferred is a pH value of about 3.

As stated, mercury halides present in the test gas stream are reduced to metallic mercury when the test gas stream is brought into contact with the condensate of the test gas stream. The mercury which is formed is then removed from the liquid phase by the gas flow of the non-condensed portion of the test gas stream through and then out of the condensate. Only in the case of a very low volume of gas flow and when larger volume areas of condensate are not reached by the gas flow, it may be necessary to force the formed mercury out of the liquid phase by supplying an additional carrier gas.

To prove or determine the metallic mercury content in the non-condensable portion of the test gas stream which leaves the condensate, known methods of analysis can be used. Quite suitable is the atom absorption spectroscopy method discussed in the aforementioned DE-OS 37 04 533. Furthermore, mass spectroscopy can be used, and this is especially advantageous, for example, when still other waste gas components are to be monitored.

An apparatus for carrying out the process of the present invention comprises a cooling chamber, which can be filled with condensate, a means to hold the filling level of the cooling chamber constant by withdrawing condensate, and a supply line for the test gas sampling stream, which ends in the liquid condensate phase. This is the place where the sampling stream condenses. The cooling chamber for the condensate can be either enclosed by a cooling jacket or have cooling coils or cold fingers in the interior.

The simplest method for holding the condensate level constant is to provide the cooling chamber with an overrun. Preferably, the overrun is attached in such a manner that the liquid condensate phase is also held or maintained in motion by the streaming condensate. The place at which the sampling stream condenses preferably is to be a specific distance away from the place at which the condensate drains through the overrun. In this manner it is achieved that there is always fresh condensate for the reduction of the mercury halides. However, the filling level of the condensate can also be held constant by other conventional methods, e.g., with a pump, controlled by a level switch. The end of the supply line for the sampling test gas stream ends preferably below the condensate level, held constant, and is designed as a gas filter.

The non-condensable portion of the test gas sampling stream, including the metallic mercury contained therein, leave the cooling chamber through a gas line, which is attached in the upper region of the cooling chamber and is adequately protected against drawing the liquid phase.

In particular, at low condensate temperatures it is recommended that this gas line be heated. The metallic, gaseous mercury is fed to the mercury analyzer through this gas line.

The process of the invention is suited for monitoring the waste gas of incinerator plants, in which the emission of mercury halides nust be taken into account and, in particular for refuse incinerator plants. Thus, it is irrelevant whether, in addition to mercury halides, there is still metallic, gaseous mercury in the waste gas stream. As suitable tests have shown, mercury is emitted from incinerator plants usually as metallic mercury and/or as mercury halide. By means of the process according to the present invention, mercury halides are reliably reduced to metallic mercury so that the entire mercury emission can be detected by determining the amount of mercury independently of the chemical form of the mercury.

The invention is now explained in detail with the aid of the figures and an example.

Figure 1:
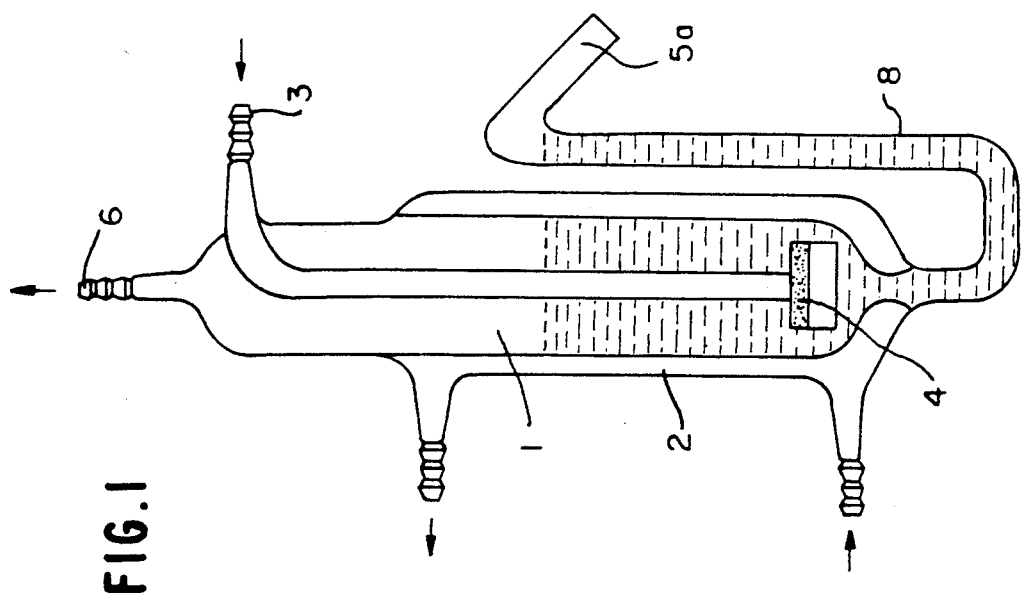
FIG. 1 shows one embodiment of an apparatus according to the present invention for carrying out the process according to the present invention.
Figure 3A:
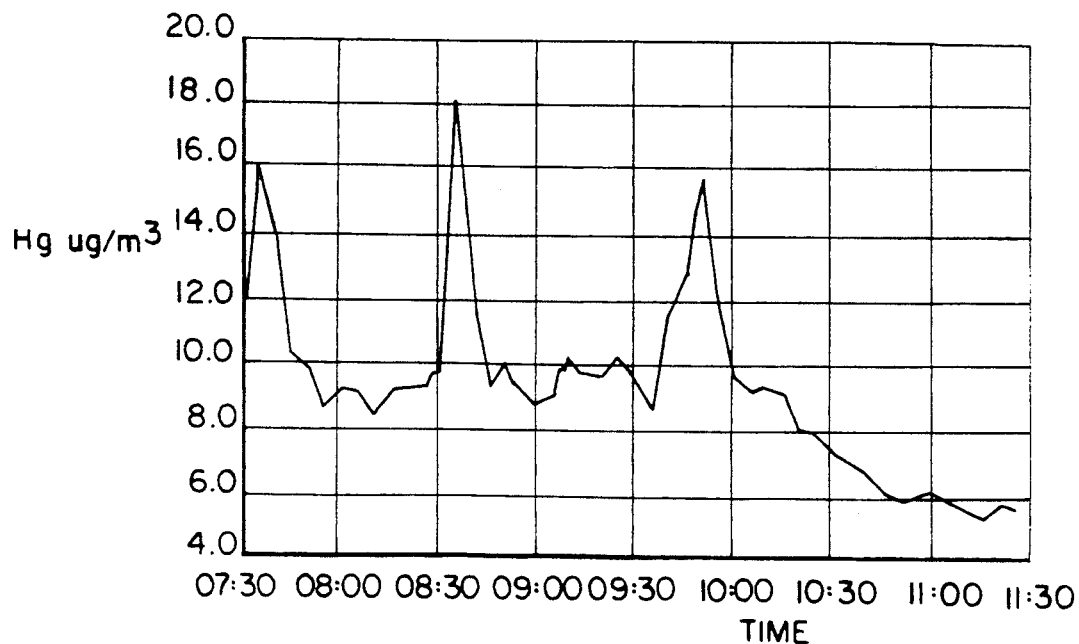
FIG. 3a shows one characteristic curve as a function of time of the mercury emission at the TAMARA refuse incinerator of Kernforschungszentrum Karlsruhe.
Figure 3B:
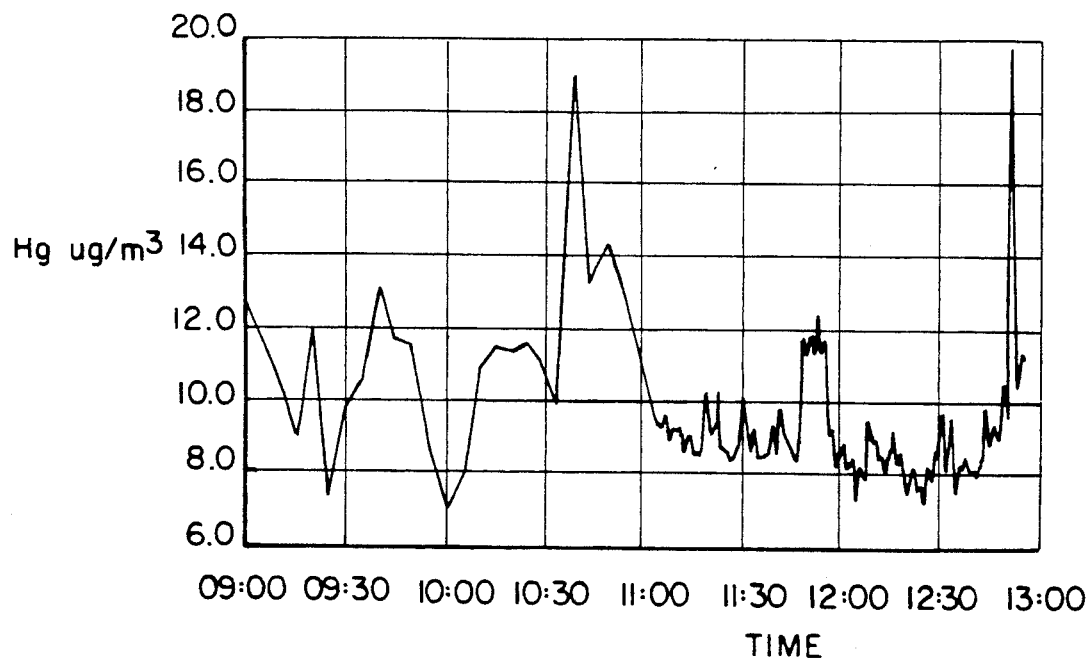
FIG. 3b shows another characteristic curve as a function of time of the mercury emission at the TAMARA refuse incinerator of Kernforschungszentrum Karlsruhe.

The apparatus according to FIGS. 1 and 2 have a cooling chamber 1 that is enclosed by a cooling jacket 2 and accommodates the condensate. A supply line 3 for the test gas stream ends in a gas filter 4 below the condensate level held constant by a condensate overrun 5a in FIG. 1 and 5b in FIG. 2.

The test gas stream flows through an exit gas line 6 into a mercury analyzer (not shown). The test gas stream is transported into cooling chamber 1 with the aid of a pump (not shown).

In FIG. 1, overrun 5a is formed by a U-shaped pipe 8, which extends from the bottom of cooling chamber 1. The apparatus according to FIG. 1 can be used when the pressure in the waste gas or sampling stream is less than or equal to the atmospheric pressure.

In FIG. 2, overrun 5b is formed by a pipe 9, which extends from a center portion of cooling chamber 1. The apparatus according to FIG. 2 can be used when the pressure in the waste gas or sampling stream is greater than or equal to the atmospheric pressure.

EXAMPLE

In the following experiments using the apparatus of FIG. 1, the process of the present invention is compared with the results of a discontinuous sampling.

The sampling takes place at the stack of the TAMARA refuse incinerator plant of Kernforschungszentrum Karlsruhe, which was driven at a throughput of 200 kg of household garbage per hour.

In accordance with the present invention, the test gas stream was cooled to a temperature of 10° C. At this temperature condensate formed at a rate of about 0.015 liters/hour. The volume of condensate in the cooled condensate chamber was held at 0.1 liters.

The pH value of the condensate during the entire test was 3.

The non-condensed portions of the test gas stream, which contained the originally present and the newly formed metallic mercury, were directed into a cuvet at atmospheric pressure. With the aid of atom absorption spectroscopy, the mercury content was continuously measured at a wavelength of 253.7 nm.

The measured mercury values were stored with the aid of a computer and totalled over a period of four hours.

The following Table shows these totalled measured values for four different runs which were made according to the present invention, with each run lasting four hours.

At the same time a second, equally large test gas stream was sampled at the stack with a second heatable probe.

This test gas stream was guided for four hours over a combination of Dowex 1×8 solid absorber and iodized active carbon. The anion exchanger is suitable in an excellent manner for selective deposit of $HgCl_2$, whereas the iodized active carbon is a sorption agent for all mercury, combined with Dowex correspondingly for metallic Hg. After the four hour run was completed, the loaded solid adsorbers were subsequently chemically analyzed for mercury. The analysis results are also shown in the Table.

The results obtained from both measurement methods correspond well with one another.

TABLE

| Test Run No. | Detected Volume of Flue Gas in Liters | Process of the Present Invention, Continuously Measuring, Summation Over for 4 hours in $\mu g/m^3$ as metallic Hg | Standard Process Discontinuously Measuring 4 hours' values in $\mu g/m^3$ Hg halides | metallic Hg |
|---|---|---|---|---|
| 1 | 428 | 8 | 8 | 1 |
| 2 | 376 | 10 | 8 | <1 |
| 3 | 454 | 9 | 7 | 1 |
| 4 | 441 | 9 | 8 | 1 |

It will be understood that the above description of the present invention is susceptible to various modifications, changes and adaptations, and the same are intended to be comprehended within the meaning and range of equivalents of the appendant claims.

What is claimed is:

1. Process for the continuous monitoring of waste gas from an incinerator plant, wherein the gas contains a reducing agent, and volatile mercury halides and optionally metallic mercury in the form of vapor, with respect to the entire mercury content of the waste gas, comprising:
    a) taking a continuous test gas stream from the waste gas,
    b) cooling the test gas stream to form a condensate which contains the reducing agent present in the waste gas and which does not contain any external reducing agent,
    c) continuously passing the test gas stream into contact with the condensate to reduce the mercury halides contained in the test gas stream to metallic mercury by the reducing agent contained in the condensate without adding any external reducing agent, and subsequently,
    d) determining the entire metallic mercury content by analysis of the test gas stream after it is passed from the condensate.

2. Process, as claimed in claim 1, wherein the test gas stream is cooled to a temperature of from 1° to 30° C.

3. Process, as claimed in claim 1, wherein the condensate is maintained at a pH value of at least 3 and at most 8.

4. Process, as claimed in claim 1, wherein the reducing agent comprises dust particles and $SO_2$ in the waste gas.

5. Apparatus for the continuous monitoring of waste gas from an incinerator plant, wherein the gas contains volatile mercury halide and optionally metallic mercury in the form of vapor, comprising:
    a) a cooling chamber for cooling and condensing a test gas stream taken from the waste gas, and for holding condensate which forms from the condensing of the test gas stream,
    b) a means for holding the condensate at a constant filling level in the cooling chamber and through which condensate is withdrawn from the cooling chamber,
    c) a supply line for introducing the test gas stream into the cooling chamber at a level below the constant filling level, and
    d) a gas line which connects the cooling chamber above the condensate level to a mercury analyzer.

6. Apparatus as claimed in claim 5, wherein the end of the supply line for the test gas stream is in the form of a gas filter.

7. Apparatus as claimed in claim 5, wherein the means for holding the condensate at a constant filling level is an overrun.

* * * * *